United States Patent
Niebauer

(10) Patent No.: US 11,696,717 B2
(45) Date of Patent: Jul. 11, 2023

(54) FREQUENCY ANALYSIS FOR PREDICTING LEFT VENTRICULAR DYSFUNCTION

(71) Applicant: THE CLEVELAND CLINIC FOUNDATION, Cleveland, OH (US)

(72) Inventor: Mark J. Niebauer, Mayfield Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 559 days.

(21) Appl. No.: 16/676,997

(22) Filed: Nov. 7, 2019

(65) Prior Publication Data

US 2020/0138321 A1    May 7, 2020

Related U.S. Application Data

(60) Provisional application No. 62/756,944, filed on Nov. 7, 2018.

(51) Int. Cl.

| | | |
|---|---|---|
| *A61B 5/0452* | (2006.01) | |
| *A61B 5/0408* | (2006.01) | |
| *A61B 5/00* | (2006.01) | |
| *G06N 20/20* | (2019.01) | |
| *A61B 5/349* | (2021.01) | |
| *A61B 5/25* | (2021.01) | |

(52) U.S. Cl.
CPC ............. *A61B 5/349* (2021.01); *A61B 5/25* (2021.01); *A61B 5/7225* (2013.01); *A61B 5/7275* (2013.01); *G06N 20/20* (2019.01)

(58) Field of Classification Search
CPC ......... A61B 5/25; A61B 5/349; A61B 5/7225; A61B 5/7253; A61B 5/7275; G06N 20/00; G06N 20/20

USPC ........................................................ 600/508
See application file for complete search history.

(56) References Cited

U.S. PATENT DOCUMENTS

| | | | |
|---|---|---|---|
| 9,586,052 B2 | 3/2017 | Gillberg et al. | |
| 2013/0296726 A1* | 11/2013 | Niebauer | A61B 5/287 600/510 |
| 2013/0310890 A1* | 11/2013 | Sweeney | A61N 1/36585 607/25 |

(Continued)

OTHER PUBLICATIONS

Buckley, Una, and Shivkumar Kalyanam. "Predictors of left ventricular dysfunction with right ventricular pacing: Is paced QRS duration the answer?." indian pacing and electrophysiology journal 15.2 (2015): 87.

(Continued)

*Primary Examiner* — Carl H Layno
*Assistant Examiner* — Jane C Kalinock
(74) *Attorney, Agent, or Firm* — Tarolli, Sundheim, Covell & Tummino LLP

(57) ABSTRACT

Systems and methods are provided for evaluating infranodal pacing is applied to a patient. Electrocardiogram (ECG) data representing the pacing is obtained from a set of electrodes as an ECG lead. A predictor value representing a frequency content a portion of the ECG lead is extracted. A fitness parameter is determined for the pacing from at least the predictor value. The fitness parameter represents a likelihood that the applied infranodal pacing will induce left ventricular dysfunction in the patient. The fitness parameter is displayed to a user at an associated display.

18 Claims, 5 Drawing Sheets

(56) References Cited

U.S. PATENT DOCUMENTS

2015/0327776 A1* 11/2015 Zhang ................... A61B 7/04
                                                                          600/300
2017/0354365 A1* 12/2017 Zhou ..................... A61N 1/395

OTHER PUBLICATIONS

Kiehl, Erich L., et al. "Incidence and predictors of right ventricular pacing-induced cardiomyopathy in patients with complete atrioventricular block and preserved left ventricular systolic function." Heart Rhythm 13.12 (2016): 2272-2278.

Mond, Harry G., and Alessandro Proclemer. "The 11th world survey of cardiac pacing and implantable cardioverter-defibrillators: calendar year 2009—a World Society of Arrhythmia's project." Pacing and clinical electrophysiology 34.8 (2011): 1013-1027.

\* cited by examiner

FREQUENCY ANALYSIS FOR PREDICTING LEFT VENTRICULAR DYSFUNCTION

This application claims priority from U.S. Provisional Patent Application Ser. No. 62/756,944, filed 7 Nov. 2018 and titled "FREQUENCY ANALYSIS TOOL FOR PREDICTING PATIENTS WHO ARE LIKELY TO DEVELOP LEFT VENTRICULAR DYSFUNCTION AFTER RIGHT VENTRICULAR PACEMAKER", the subject matter of which is incorporated hereby incorporated by reference in its entirety.

FIELD OF THE INVENTION

The present invention relates to systems and methods for regulating the function of a heart in a living being and, in particular, is directed to systems and methods utilizing frequency analysis of an ECG lead to predict which patients are likely to experience left ventricular dysfunction during infranodal cardiac pacing.

BACKGROUND OF THE INVENTION

Pacing-induced cardiomyopathy can occur in patients receiving right ventricular (RV) pacing that have preserved left ventricle ejection fraction (LVEF) at the time of implant due to the high pacing percentage necessary to address conditions such as a left bundle block. The introduction of right ventricular (RV) pacing has been found to produce some degree of left ventricular (LV) dysfunction in between twelve and seventeen percent of patients having a normal LVEF at baseline. For patients who are already experiencing some degree of LV dysfunction, the risk is significantly higher, and the introduction of RV pacing can result in further loss of LV function.

SUMMARY OF THE INVENTION

In accordance with an aspect of the present invention, a method includes applying infranodal pacing to a patient at a pacing site. Electrocardiogram (ECG) data representing the pacing site is obtained from a set of electrodes as an ECG lead. A predictor value representing a frequency content a portion of the ECG lead is extracted. A fitness parameter is determined for the pacing site from at least the predictor value. The fitness parameter represents a likelihood that the infranodal pacing applied at the pacing site will induce left ventricular dysfunction in the patient. The fitness parameter is displayed to a user at an associated display.

In accordance with another aspect of the present invention, a system includes a signal processor configured to receive an ECG lead and isolate a portion of interest from the ECG lead during infranodal pacing of a patient. A predictor extraction component is configured to extract a predictor value representing a frequency content of the portion of interest. A parameter calculation component is configured to determine a parameter representing the likelihood that the patient will experience left ventricular dysfunction induced by the infranodal pacing from at least the predictor value.

In accordance with yet another aspect of the present invention, a method is provided for evaluating an infranodal pacing method in accordance with an aspect of the present invention. Infranodal pacing is applied to a patient using a first pacing method. Electrocardiogram (ECG) data representing the first pacing method is obtained from a set of electrodes as a first ECG lead. A predictor value is extracted representing a frequency content of a QRS complex of the first ECG lead. A fitness parameter is determined for the first pacing method from at least the first predictor value. The fitness parameter represents a likelihood that the infranodal pacing using the first pacing method will induce left ventricular dysfunction in the patient. A second pacing method is selected for the patient if the fitness parameter does not meet a threshold value.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Systems and methods are provided herein for the use of the frequency content of the QRS complex during infranodal pacing to predict the likelihood that the infranodal pacing will induce left ventricular dysfunction. By "infranodal pacing," it is meant any pacing that falls below the atrioventricular node and provides ventricular activation, including right ventricular pacing, left ventricular pacing, biventricular pacing, and His-bundle pacing. The frequency content of an electrocardiogram (ECG) signal, referred to as a lead, captured during infranodal pacing can be analyzed and used to predict if a patient is likely to develop left ventricular dysfunction given a infranodal pacing applied in a specific location. This can be used during implantation of the pacemaker as an objective aid to select the most effective infranodal pacing method and associated site of those available for the individual patient.

In one example, frequency analysis of the QRS complex in can be performed, for example, via a Fourier transform, time-frequency analysis, wavelet analysis, or a similar process, to determine one or more features that can be used for predicting the response of a patient to infranodal pacing. Features determined from the frequency analysis can include, for example, a fundamental frequency of the QRS complex as well as a measure of change of a median frequency throughout the QRS complex. This can be performed for multiple locations to select an infranodel pacing location that minimizes the likelihood of left ventricular dysfunction.

Figure 1:
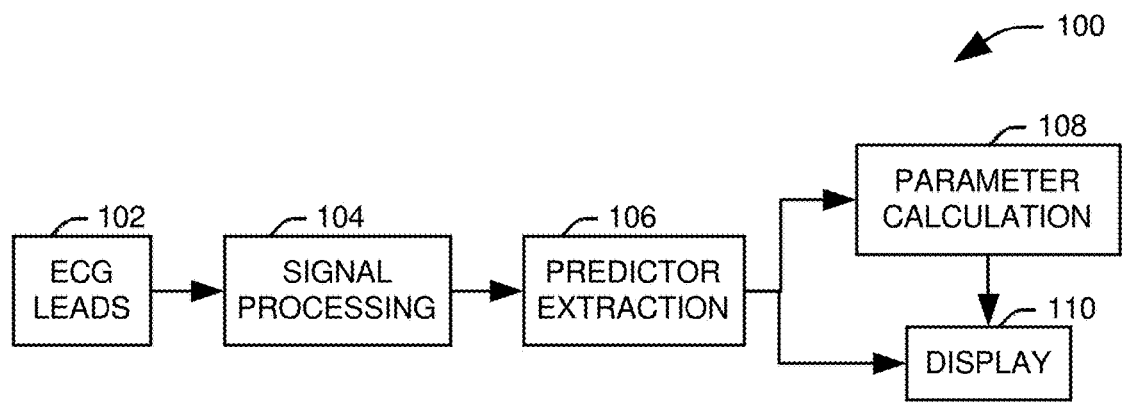
FIG. 1 illustrates one example of a system for predicting the likelihood that infranodal pacing will induce left ventricular dysfunction in a patient in accordance with an aspect of the present invention.

FIG. 1 illustrates a system 100 for predicting the likelihood that infranodal pacing will induce left ventricular dysfunction in a patient in accordance with an aspect of the present invention. In the illustrated implementation, the system 100 is a stand-alone module that obtains electrocardiogram (ECG) signals through a set of ECG electrodes 102. It will be appreciated, however, that the system 100 could be implemented as machine executable instructions provided to an existing ECG apparatus, and utilize electrodes and signal processing components (e.g., filtering components, etc.) associated with that apparatus. The system can also be implemented as executable instructions provided to a cardiac rhythm management device, such as a pacemaker. Regardless of the specific implementation, the electrodes 102 can be arranged with any standard or specialized surface lead position.

The ECG leads from the electrodes is provided to a signal processing component 104 to condition the signal and isolate any portions of the signal of interest for the analysis. In one implementation, the signal processing component 104 can isolate a QRS complex from each of a proper subset of the ECG leads, for example, from leads I, AVF, and V3. The signal processing component 104 can include one or both of analog and digital filtering components to remove noise and/or pacing artifact from the ECG signals. The signal isolation process can be assisted by an operator or completely automated, depending on the implementation of the system.

A predictor extraction component 106 extracts a predictor value representing a frequency component of the ECG data from the processed data. For example, a frequency analysis of the ECG signal on one or more leads can be performed to provide a frequency domain representation of the signal, with the parameters drawn from the frequency domain representation. In one embodiment of the present invention, the frequency analysis is performed using a fast Fourier transform (FFT). In another embodiment of the present invention, the frequency analysis is performed using the Welch periodogram. In still another embodiment of the present invention, the frequency analysis is performed using autoregressive power spectrum (AR) analysis. In yet another embodiment, the frequency analysis is performed via a wavelet transformation of the ECG data. In still another embodiment, the frequency analysis is performed using time-frequency analysis. It will be appreciated that selected predictors can include, for example, a fundamental frequency in a selected portion of the ECG data, a change in the median frequency of the ECG data across the same or a different selected portion of the ECG data, or any other appropriate parameters representing the frequency.

In one example, the feature extractor 106 can include dedicated hardware or machine readable instructions stored on a non-transitory computer readable medium for performing a continuous or discrete Fourier transform. The inventors have determined that patients who are likely to experience LV dysfunction over time from RV pacing tend to have a paced QRS complex with a lower fundamental frequency than patients for whom LV dysfunction does not develop, and that the median frequency of the QRS complex decreases, as opposed to increases, during the QRS complex. Accordingly, the onset of LV dysfunction induced by RV pacing can be predicted from the spectral content of the QRS complex from a given patient. In this example, the fundamental frequency of the QRS complex, for example, from a V3 lead, along with a measure of the slope of the median frequency across the QRS complex can be extracted for the patient at each of a plurality of infranodal pacing sites.

The extracted predictors are provided to a parameter calculation component 108 which determines a parameter representing the likelihood that the patient will experience left ventricular dysfunction given infranodal pacing at a given pacing site. The parameter calculation component 108 can, for example, include an expert system or group of expert systems configurable to determine the effectiveness of a proposed infranodal pacing site for a patient. Examples of suitable systems can include artificial neural networks, support vector machines, Hidden Markov Models, rule based expert systems, and regression models, although any of a number of supervised or unsupervised learning algorithms can be used at the parameter calculation component 108. Alternatively, the parameter calculation component 108 can simply calculate a function of the predictor value, such as a linear function or a step function, that provides a useful continuous or categorical metric for decision-making for a clinician. It will be appreciated that additional features unrelated to the frequency can be used for parameter calculation, including biometric parameters of the patient. It will be appreciated that data from the various leads can be used for extracting frequency spectra, such that features representing a given patient can be drawn from multiple frequency spectra representing multiple leads. In one implementation, information from different leads can be weighted differently. For example, the inventors have found information from lead V3 to be of particular value, and this increased value may be reflected in the operation of the parameter calculation component 108.

The predictor values, along with an associated result from the parameter calculation component 108, can be displayed at an associated display 110. In one implementation, the frequency spectra associated with each of a plurality of pacing sites can be displayed along with associated metrics from the parameter calculation component 108 to allow a user to compare the values to select an optimum site for the application of infranodal pacing that minimizes the likelihood of left ventricular dysfunction. Accordingly, the determination of the optimal site can be made by the operator from the displayed frequency spectra, completely automated, or made by operator guided by results from the parameter calculation component 108.

Figure 2A:
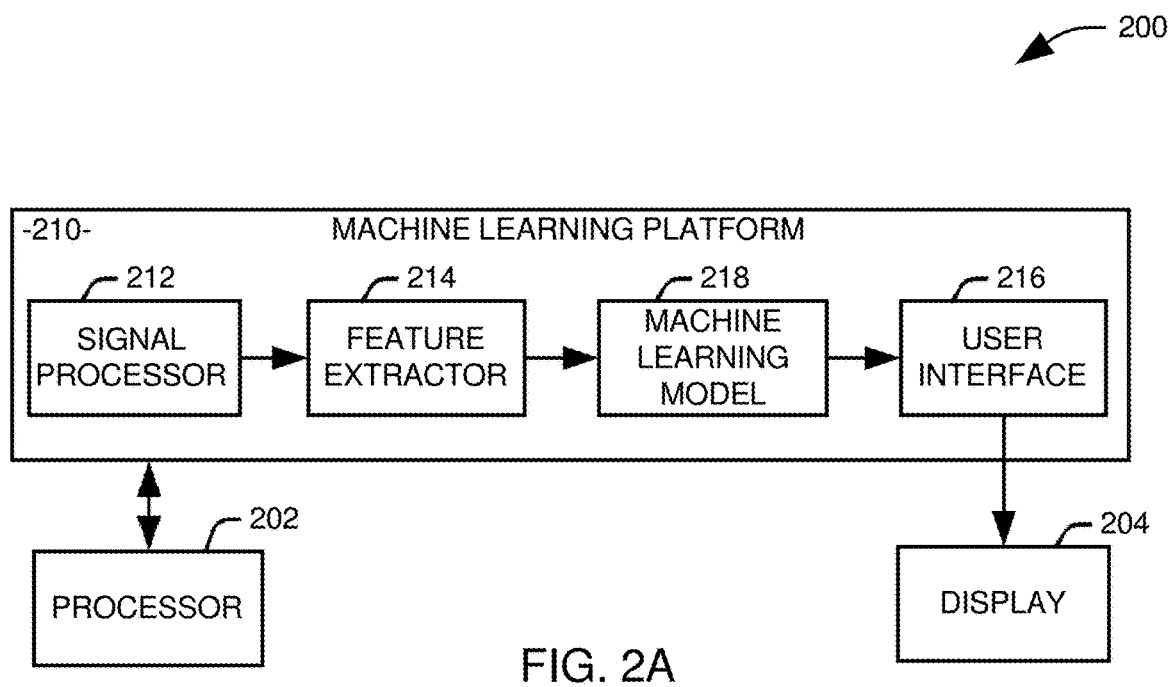
FIG. 2A illustrates one implementation of a system for predicting the likelihood that infranodal pacing will induce left ventricular dysfunction in a patient in accordance with an aspect of the present invention.

FIG. 2A illustrates another example of a system 200 for predicting the likelihood that infranodal pacing will induce left ventricular dysfunction in a patient in accordance with an aspect of the present invention. The system 200 includes a processor 202, a display 204, and a non-transitory computer readable medium 210 storing machine executable instructions for receiving and evaluating received ECG signals during infranodal pacing to determine the likelihood that the infranodal pacing at a selected site will induce left ventricular dysfunction in a patient. The executable instructions include a signal processor 212 to receive ECG data for the patient during infranodal pacing, condition the signal, and isolate any portions of the signal of interest for the analysis.

Figure 2B:
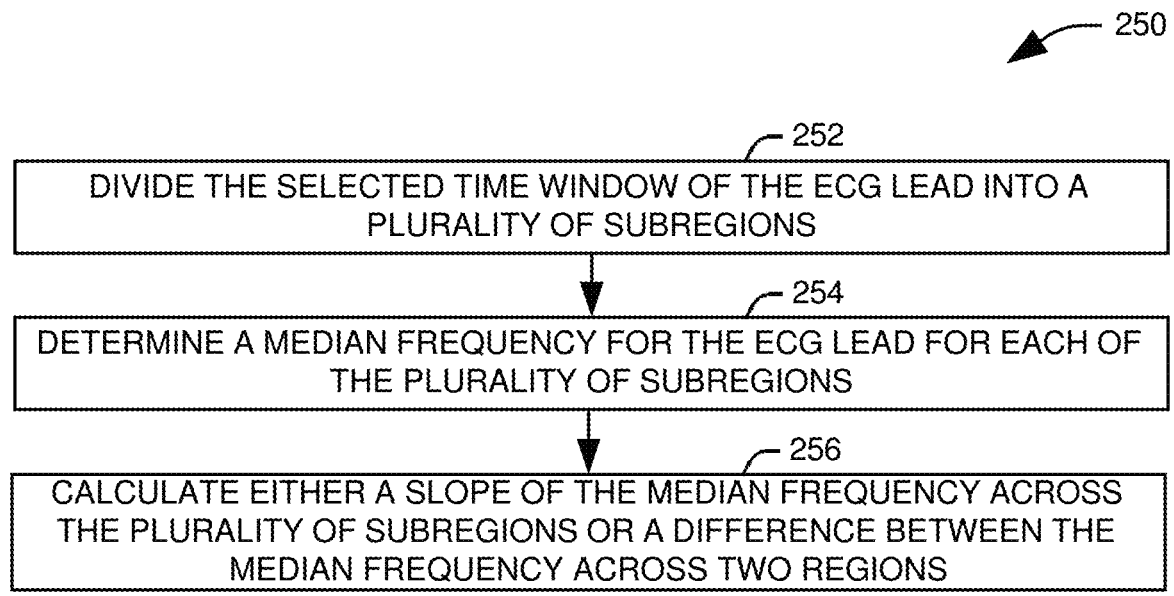
FIG. 2B illustrates a method 200 for determining a change in the median frequency for an example time window of an ECG lead, illustrated as FIG. 2C.
Figure 2C:
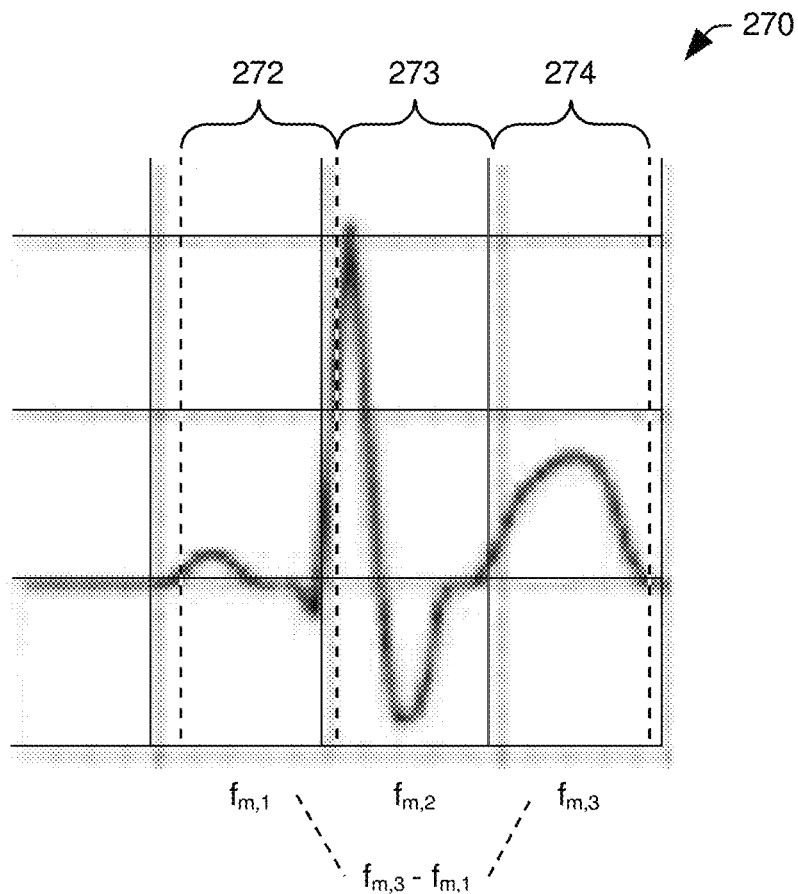

A feature extractor 214 extracts a set of at least one feature from the ECG signals representing the frequency content of the signals. For example, a frequency analysis of the ECG signal on one or more leads can be performed to provide a frequency domain representation of the ECG signal, with the parameters drawn from the frequency domain representation. It will be appreciated that selected features can include a median or fundamental frequency in a selected portion of the ECG data, a change in the median or fundamental frequency of the ECG data across the same or a different selected portion of the ECG data, or any other appropriate parameters representing the frequency. FIG. 2B illustrates a method 200 for determining the change in the median frequency for an example time window 270 of an ECG lead, illustrated as FIG. 2C. At 252, the time window of the ECG lead is divided into a plurality of subregions 272-274. At 254, a median frequency, $f_m$, of the ECG signal for each subregion is determined. At 256, either a slope of the median frequency across the subregions or a difference between the median frequency for several regions is calculated at 254. In the illustrated example, a difference between a median frequency, $f_{m,1}$, of the first subregion 272 and a median frequency, $f_{m,3}$, of the third subregion 274 is calculated, but it will be appreciated that this is merely a simplified example, and that the features can include multiple differences, different numbers of subregions, or a slope calculation. It will be appreciated that the difference calculation can be performed by providing median or fundamental frequencies for several subregions to a machine learning model. For example, in a regression analysis, the difference calculation can be implicit in the calculation of the regression coefficient.

The feature extractor 214 can also obtain one or more biometric parameters representing the patient, for example, an age of the patient, a sex of the patient, a duration of a QRS complex associated with the patient, a baseline left ventricle ejection fraction (LVEF), and an LVEF during pacing. The feature extractor 214 can, for example, retrieve the biometric parameters from an electronic health records database, receive them from a user via a user interface 216, or obtain them from an imaging system (not shown) used to determine the LVEF prior to or during RV pacing.

The extracted features are provided to a machine learning model 218 that generates a clinical parameter representing a likelihood that the patient will develop LV dysfunction in response to RV pacing at a given site. The machine learning model 218 can utilize one or more pattern recognition algorithms, implemented, for example, as classification and regression models, each of which analyze the extracted feature vector to assign a clinical parameter to the user. It will be appreciated that the clinical parameter can be categorical or continuous. Where multiple classification and regression models are used, the machine learning model 218 can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

A classification can also be performed across multiple stages. In one example, an a priori probability can be determined for a clinical parameter without the values representing the frequency content of a given site, for example, based upon the biometric parameters for the patient. A second stage of the model can use the values derived from the frequency content of the ECG signal, and, optionally, additional values, to generate a value for the clinical parameter. A known performance of the second stage of the machine learning model, for example, defined as values for the specificity and sensitivity of the model, can be used to update the a priori probability given the output of the second stage.

The machine learning model 218, as well as any constituent models, can be trained on training data representing the various outcomes of interest. For example, each instance of training data can represent a given patient according to the set of extracted features and a categorical or continuous label. For example, each instance can be labeled with a class (e.g., an "experienced LV dysfunction" class or a "did not experience LV dysfunction" class) or a continuous value, such as a loss of LVEF from a baseline value prior to RV pacing. The training process of the machine learning model 218 will vary with its implementation, but training generally involves a statistical aggregation of training data into one or more parameters associated with the output classes. Any of a variety of techniques can be utilized for the models, including support vector machines, regression models, self-organized maps, k-nearest neighbor classification or regression, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A k-nearest neighbor model populates a feature space with labelled training samples, represented as feature vectors in the feature space. In a classifier model, the training samples are labelled with their associated class, and in a regression model, the training samples are labelled with a value for the dependent variable in the regression. When a new feature vector is provided, a distance metric between the new feature vector and at least a subset of the feature vectors representing the labelled training samples is generated. The labelled training samples are then ranked according to the distance of their feature vectors from the new feature vector, and a number, k, of training samples having the smallest distance from the new feature vector are selected as the nearest neighbors to the new feature vector.

In one example of a classifier model, the class represented by the most labelled training samples in the k nearest neighbors is selected as the class for the new feature vector. In another example, each of the nearest neighbors can be represented by a weight assigned according to their distance from the new feature vector, with the class having the largest aggregate weight assigned to the new feature vector. In a regression model, the dependent variable for the new feature vector can be assigned as the average (e.g., arithmetic mean) of the dependent variables for the k nearest neighbors. As with the classification, this average can be a weighted average using weights assigned according to the distance of the nearest neighbors from the new feature vector. It will be appreciated that k is a metaparameter of the model that is selected according to the specific implementation. The distance metric used to select the nearest neighbors can include a Euclidean distance, a Manhattan distance, or a Mahalanobis distance.

A regression model applies a set of weights to various functions of the extracted features, most commonly linear functions, to provide a continuous result. In general, regression features can be categorical, represented, for example, as zero or one, or continuous. The machine learning model 218 can be implemented as a linear combination of the values of the extracted features. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task. Regardless of the specific model employed, the clinical parameter generated at the machine learning model 218 can be provided to a user at the display 204 via the user interface 216 or stored at the non-transitory computer readable medium 210, for example, in an electronic medical record associated with the patient.

In one implementation, the machine learning model 218 can be applied to frequency data retrieved from each of a plurality of RV pacing sites to allow a user to compare the values to select an optimum site for the application of infranodal pacing or determine if a different method of infranodal pacing would be beneficial. Accordingly, the determination of the optimal site can be completely automated or made by an operator guided by results from the machine learning model. It will be appreciated that the machine learning model 218 can include multiple machine learning models that are selected according to a categorical feature of the patient, which may utilize different features from the feature extractor 214. In one example, a first model can be selected if the patient has a LVEF in a first range, and a second model can be selected if the patient has an LVEF outside of the first range. Table 1 illustrates exemplary features that could be used for a first model, representing patients with an LVEF between fifty and sixty percent who are receiving right ventricular pacing, and Table 2 illustrates features for a second, more general, model that can be used for patients not falling within this range.

TABLE 1

| | Normal (n = 41) | CM (n = 44) | Univariate P | Multivariate P | AUC |
|---|---|---|---|---|---|
| Age (y) | 67.9 ± 11.4 | 72.5 ± 10.2 | 0.071 | — | — |
| Gender (m/F) | 21/20 | 25/19 | 0.605 | — | — |
| QRSd (ms) | 164.9 ± 27.6 | 172.7 ± 17.4 | <0.05 | 0.078 | 0.644 |
| Initial LVEF (%) | 56.3 ± 3.0 | 54.5 ± 3.3 | <0.01 | 0.051 | 0.663 |
| Change in median QRS Frequency (Hz)* | 0.208 ± 0.544 | −0.199 ± 0.537 | <0.001 | <0.01 | 0.705 |

*Change in the median frequency of the second half of the QRS compared to the first half

TABLE 2

| | Normal (n = 61) | CM (n = 49) | Univariate P | Multivariate P | AUC |
|---|---|---|---|---|---|
| Age (y) | 70.1 ± 11.1 | 72.5 ± 10.2 | 0.242 | — | — |
| Gender (m/F) | 30/31 | 28/21 | 0.406 | — | — |
| QRSd (ms) | 164.4 ± 16.8 | 172.2 ± 16.6 | <0.02 | 0.067 | 0.647 |
| Initial LVEF (%) | 59.2 ± 5.2 | 55.5 ± 4.5 | <0.001 | 0.002 | 0.718 |
| Change in median QRS Frequency (Hz)* | 0.139 ± 0.505 | −0.193 ± 0.588 | <0.002 | <0.01 | 0.660 |

*Change in the median frequency of the second half of the QRS compared to the first half.

Figure 3:
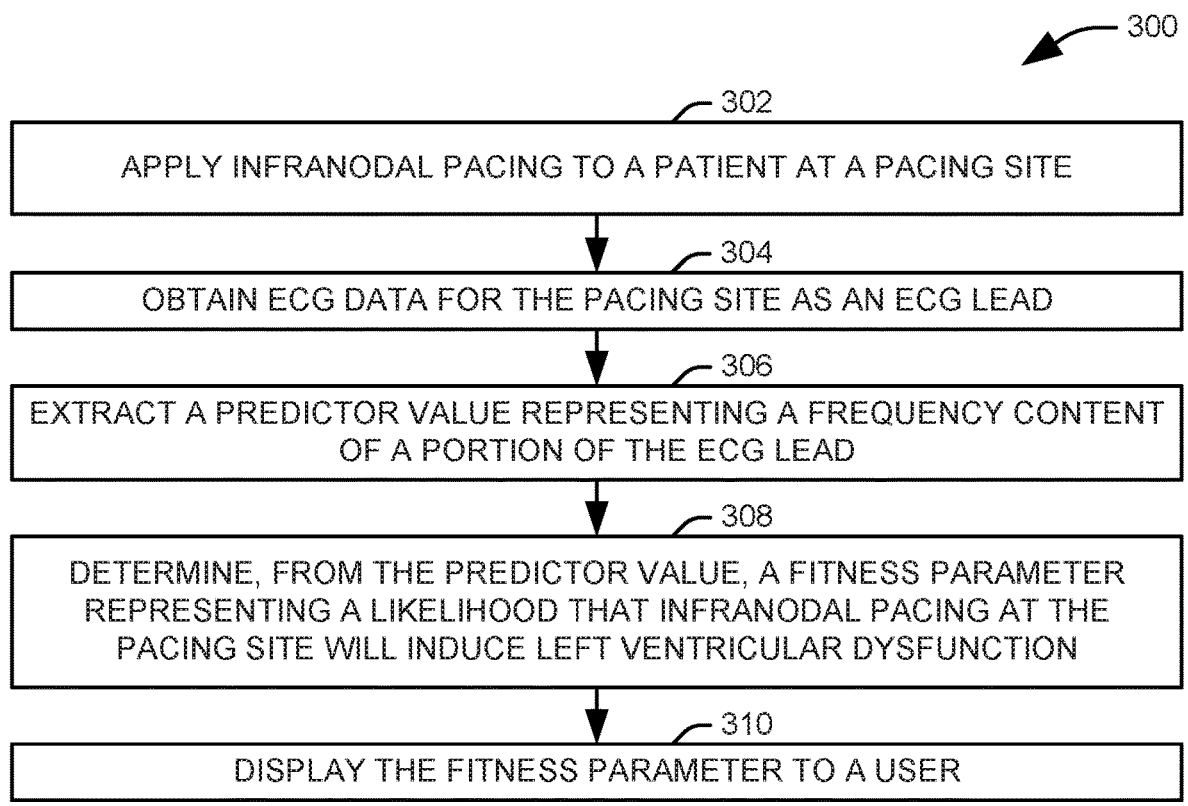
FIG. 3 illustrates a method for determining the likelihood that a patient will develop left ventricular dysfunction in response to infranodal pacing in accordance with an aspect of the present invention.
Figure 4:
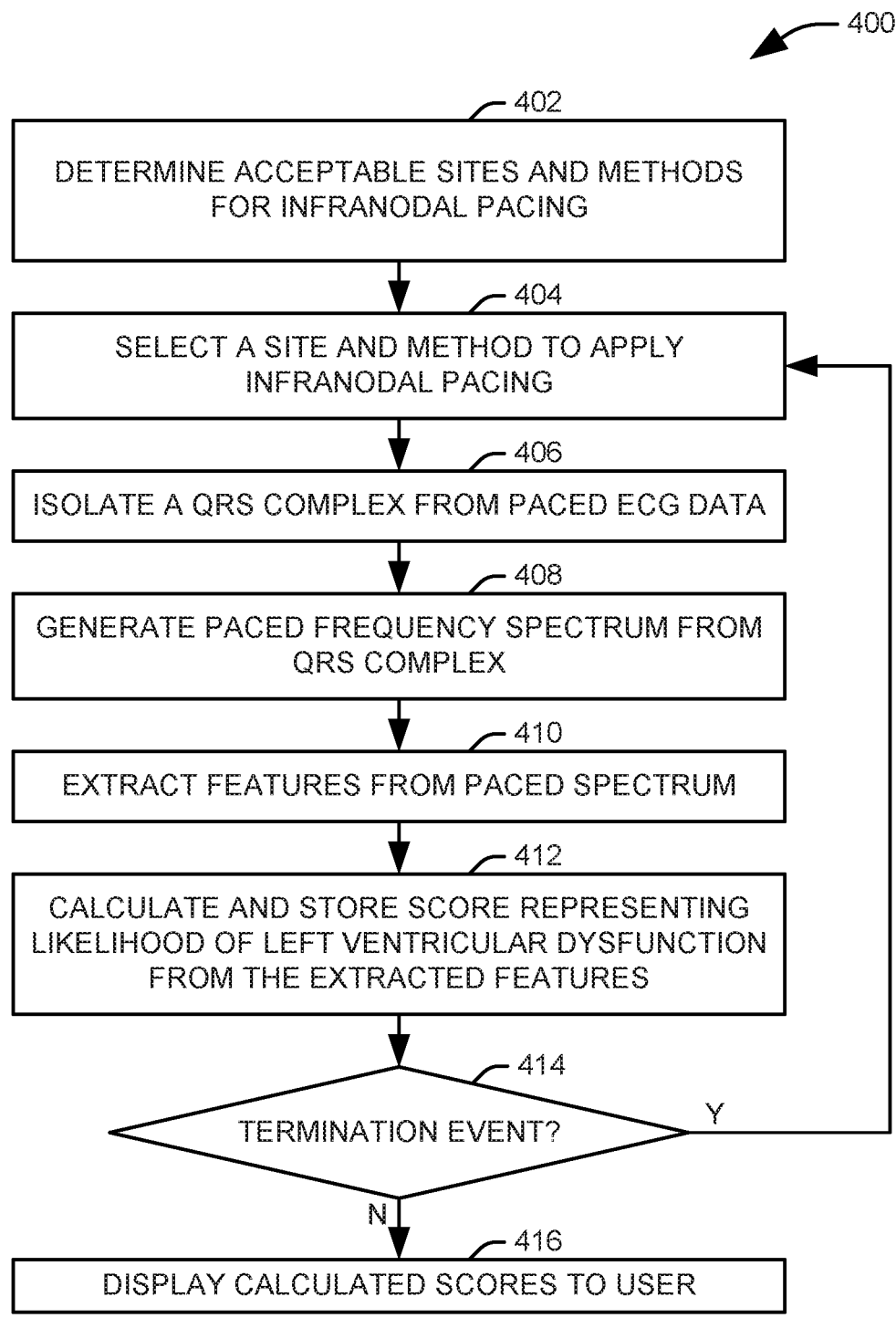
FIG. 4 illustrates a method for determining a best site for infranodal pacing to minimize a risk of left ventricular dysfunction in accordance with an aspect of the present invention.
Figure 5:
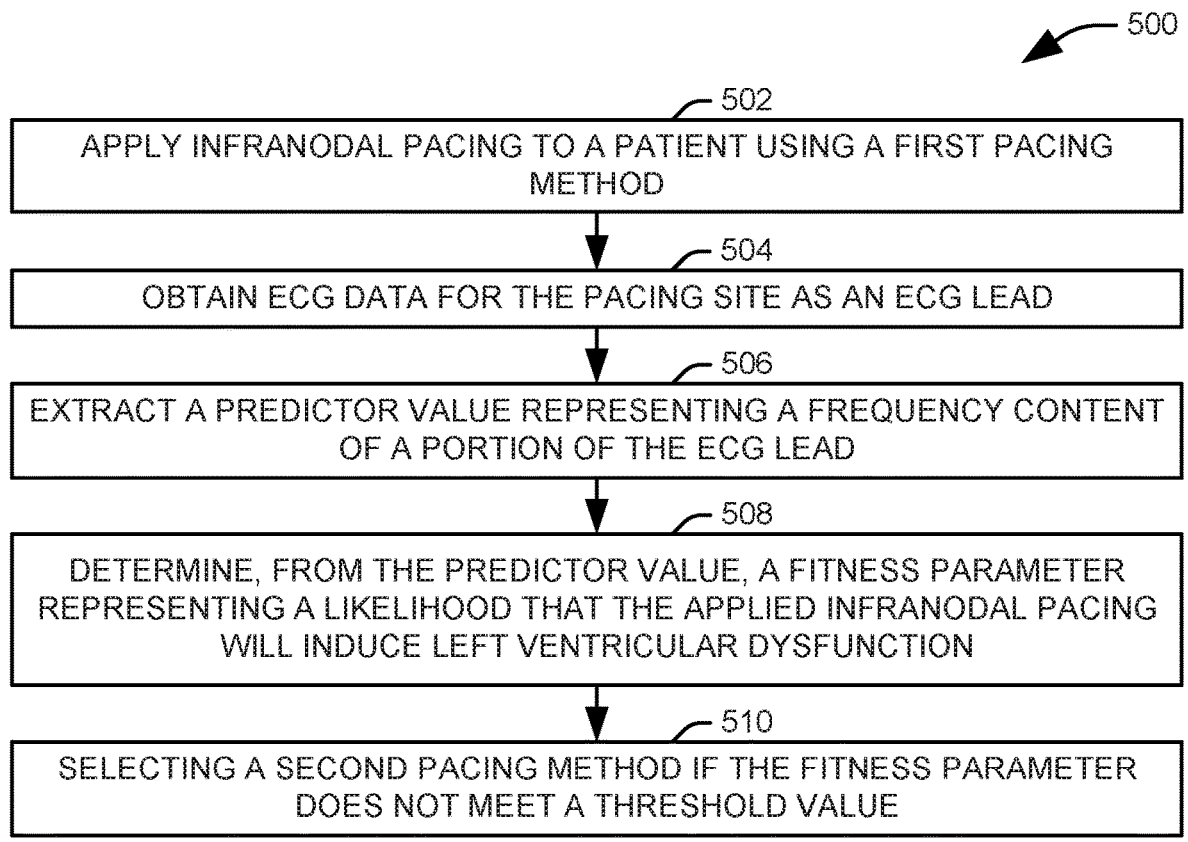
FIG. 5 illustrates a method for evaluating an infranodal pacing method in accordance with an aspect of the present invention.

In view of the foregoing structural and functional features described above, methods in accordance with various aspects of the present invention will be better appreciated with reference to FIGS. 3-5. While, for purposes of simplicity of explanation, the methods of FIGS. 3-5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect of the present invention.

FIG. 3 illustrates a method 300 for determining the likelihood that a patient will develop left ventricular dysfunction in response to infranodal pacing in accordance with an aspect of the present invention. At 302, infranodal pacing is applied to a patient at a pacing site. At 304, electrocardiogram (ECG) data representing the pacing site is obtained from a set of electrodes as an ECG lead. It will be appreciated that ECG data can be collected for multiple infranodal pacing sites, with the analysis steps at 306 and 308 performed for each pacing site to determine a pacing site with a lowest likelihood of inducing left ventricular dysfunction.

At 306, a predictor value representing a frequency content of the ECG lead is extracted from the ECG data. In one example, a QRS complex is isolated as the portion of the ECG lead, and the predictor value is extracted to represent a frequency component of the isolated QRS complex. The predictor value can include any appropriate measure of the frequency content of the selected portion of the ECG lead, and can include, for example, a fundamental frequency of a portion of the ECG lead or a change in the median frequency across a portion of the ECG lead. In one implementation, the change in the median frequency across a portion of the ECG lead can be determined by dividing the portion of the ECG lead into a plurality of regions and calculating a slope of the median frequency across the QRS complex. Alternatively, the change in the median frequency can be determined as a difference between a median frequency of a second half of the portion of the ECG lead and a median frequency of a first half of the portion of the ECG lead.

At 308, a fitness parameter is determined for the pacing site from at least the predictor value. The fitness parameter represents a likelihood that the infranodalpacing applied at the pacing site will induce left ventricular dysfunction in the patient. In one implementation, the fitness parameter for the pacing site is determined by providing the predictor value to a machine learning model. Alternatively, the predictor value or a function of the predictor can be used as extracted as a measure of the fitness of the pacing site. In one implementation, biometric parameters that do not represent a frequency component of the portion of the ECG lead, such as a QRS duration, a left ventricular ejection fraction, an age of the patient, or a similar value, can be used in addition to any extracted predictor values. These values can be used as additional features for a machine learning model or, in one example, to select among multiple machine learning models. For example, a first machine learning model when a given biometric parameter is within a first range, and a second machine learning model can be used when the biometric parameter is within a second range. At 310, the fitness parameter is displayed to the user at an associated display.

FIG. 4 illustrates a method 400 for determining a best site for infranodal pacing to minimize a risk of left ventricular dysfunction in accordance with an aspect of the present invention. At 402, a plurality of acceptable sites and methods for applying infranodal pacing to the ventricle are determined. A clinician can determine one or more types of infranodal pacing, such as left ventricular pacing, right ventricular pacing, biventricular pacing, and His-bundle pacing, that may be effective for a given patient. For each of these pacing methods, a number of anatomically available sites can be determined from imaging of the chest cavity. At 404, a pacing method and associated site is selected and the selected pacing is applied to the patient at the selected site. At 406, at least one QRS complex is isolated from ECG data from the patient. In one implementation, the QRS complex from the V3 lead is used, but it will be appreciated that information from different leads or multiple leads can be used.

At 408, each QRS complex is converted into the frequency domain to produce respective frequency spectra. At 410, one or more features are extracted from the frequency spectrum associated with the selected pacing site. For example, the one or more features can include a fundamental frequency associated with the QRS complex, a median power for the QRS complex, or a change in one of these values across various portions of the QRS complex. In one implementation, one feature can include a change in the median frequency across a frequency spectrum derived from the QRS complex on the V3 lead.

At 412, a score representing the effectiveness of the selected pacing site and method is calculated from the extracted features and stored. For example, the features can be provided to an expert system, such as an artificial neural network, a statistical classifier, or a support vector machine, that provides a confidence value representing the likelihood that a patient will develop left ventricular dysfunction induced by pacing at the selected pacing site. At 414, it is determined a termination condition has been achieved. For example, the method can be terminated if no additional pacing sites remain for evaluation or if the calculated score exceeds a threshold value. If not (N), the method returns to 402 to select a new pacing site and method. If so (Y), the calculated scores can be provided to a user at an associated display at 416.

FIG. 5 illustrates a method 500 for evaluating an infranodal pacing method in accordance with an aspect of the present invention. At 502, infranodal pacing is applied to a patient using a first pacing method, such as right ventricular pacing, left ventricular pacing, biventricular pacing, or His-bundle pacing. At 504, electrocardiogram (ECG) data representing the first pacing method is obtained from a set of electrodes as a first ECG lead. At 506, a predictor value is extracted representing a frequency content of a QRS complex of the first ECG lead. At 508, a fitness parameter is determined for the first pacing method from at least the first predictor value. The fitness parameter represents a likelihood that the infranodal pacing using the first pacing method will induce left ventricular dysfunction in the patient. At 510, a second pacing method is selected for the patient if the fitness parameter does not meet a threshold value.

Figure 6:
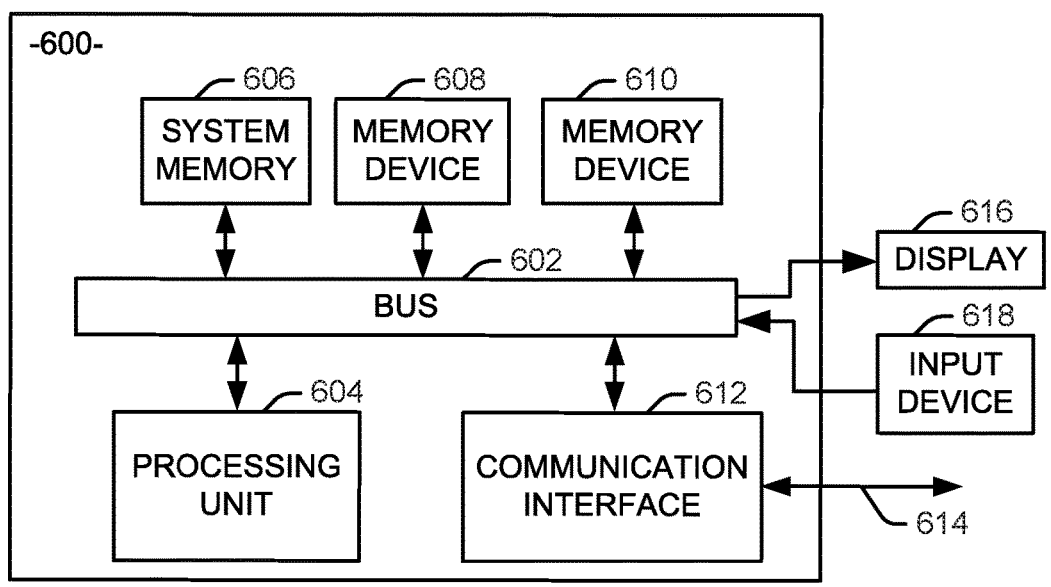
FIG. 6 is a schematic block diagram illustrating an exemplary system of hardware components capable of implementing examples of the systems and methods disclosed herein.

FIG. 6 is a schematic block diagram illustrating an exemplary system 600 of hardware components capable of implementing examples of the systems and methods disclosed herein. The system 600 can include various systems and subsystems. The system 600 can be a personal computer, a laptop computer, a workstation, a computer system, an appliance, an application-specific integrated circuit (ASIC), a server, a server BladeCenter, a server farm, etc.

The system 600 can include a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard, touch screen, and/or a mouse). The system bus 602 can be in communication with the processing unit 604 and the system memory 606. The additional memory devices 608 and 610, such as a hard disk drive, server, standalone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core.

The additional memory devices 606, 608, and 610 can store data, programs, instructions, database queries in text or compiled form, and any other information that may be needed to operate a computer. The memories 606, 608 and 610 can be implemented as computer-readable media (integrated or removable), such as a memory card, disk drive, compact disk (CD), or server accessible over a network. In certain examples, the memories 606, 608 and 610 can comprise text, images, video, and/or audio, portions of which can be available in formats comprehensible to human beings. Additionally or alternatively, the system 600 can access an external data source or query source through the communication interface 612, which can communicate with the system bus 602 and the communication link 614.

In operation, the system 600 can be used to implement one or more parts of a system for evaluating the response of a patient to infranodal pacing in accordance with the present invention, in particular, the predictor extraction component 116 and the parameter calculation component 118. Computer executable logic for implementing the system resides on one or more of the system memory 606, and the memory devices 608 and 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution. This medium may be distributed across multiple discrete assemblies all operatively connected to a common processor or set of related processors.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

Having described the invention, the following is claimed:

1. A method comprising:
    applying infranodal pacing to a patient at a pacing site;
    obtaining electrocardiogram (ECG) data representing the pacing site from a set of electrodes as an ECG lead;
    extracting a predictor value representing a frequency content of a selected time window of the ECG lead, the predictor value for the frequency content of the selected time window of the ECG lead comprising a change in the median frequency across the selected time window of the ECG lead, wherein the change in the median frequency is determined by dividing the selected time window of the ECG lead into a plurality of subregions, determining a median frequency for each subregion, and calculating one of a slope of the median frequency across the plurality of subregions and a difference between the median frequency of a first selected subregion and a second selected subregion;
    determining a fitness parameter for the pacing site from at least the predictor value, the fitness parameter representing a likelihood that the infranodal pacing applied at the pacing site will induce left ventricular dysfunction in the patient; and
    displaying the fitness parameter to a user at an associated display.

2. The method of claim 1, wherein extracting a predictor value representing the frequency content of the ECG lead comprises:
    isolating a QRS complex from the ECG lead; and
    extracting the predictor value as to represent a frequency content of the isolated QRS complex.

3. The method of claim 1, wherein the predictor value for the frequency content of the selected time window of the ECG lead is extracted as a fundamental frequency of the selected time window of the ECG lead.

4. The method of claim 1, wherein the predictor value for the frequency content of the selected time window of the ECG lead is extracted as a difference between a median frequency of a first subregion of the selected time window of the ECG lead and a median frequency of a second subregion of the selected time window of the ECG lead.

5. The method of claim 1, determining a fitness parameter for the pacing site from at least the predictor value comprises determining a fitness parameter for the pacing site from the predictor value and a biometric parameter that is not extracted from a frequency content of the ECG lead.

6. The method of claim 5, wherein the biometric parameter is a left ventricular ejection fraction of the patient.

7. The method of claim 1, wherein the ECG lead is a first ECG lead, the pacing site is a first pacing site, the predictor value is a first predictor, and the fitness parameter is a first fitness parameter and the method further comprising:
    applying infranodal pacing to the patient at a second pacing site;
    obtaining electrocardiogram (ECG) data representing the second pacing site from the set of electrodes as a second ECG lead;
    extracting a second predictor value representing a frequency content of as a selected time window of the second ECG lead;
    determining a second fitness parameter for the second pacing site from at least the extracted second predictor value, the second fitness parameter representing a likelihood that the infranodal pacing applied at the second pacing site will induce left ventricular dysfunction in the patient;
    selecting between the first pacing site and the second pacing site according to the first fitness parameter and the second fitness parameter.

8. The method of claim 1, wherein determining the fitness parameter for the pacing site from at least the extracted predictor value comprises providing the predictor value to a machine learning model.

9. The method of claim 8, wherein the predictor value is a first predictor and the method further comprising extracting a second predictor value, wherein providing the predictor value to the machine learning model comprises providing the first predictor value to a first machine learning model when the second predictor value is within a first range, and providing the second predictor value to a second machine learning model when the second predictor value is within a second range.

10. The method of claim 9, wherein the second predictor value is a left ventricular ejection fraction of the patient.

11. The method of claim 9, wherein applying infranodal pacing to the patient comprises applying right ventricular pacing to the patient.

12. A system comprising:
- a signal processor configured to receive an ECG lead and isolate a selected time window from the ECG lead during infranodal pacing of a patient;
- a predictor extraction component configured to extract a predictor value representing a frequency content of the selected time window, the predictor value for the frequency content of the portion of the ECG lead comprising a change in the median frequency across the selected time window of the ECG lead, wherein the change in the median frequency is determined by dividing the selected time window of the ECG lead into a plurality of subregions, determining a median frequency for each subregion, and calculating one of a slope of the median frequency across the plurality of subregions and a difference between the median frequency of a first selected subregion and a second selected subregion; and
- a parameter calculation component configured to determine a parameter representing the likelihood that the patient will experience left ventricular dysfunction induced by the infranodal pacing from at least the predictor value.

13. The system of claim 12, wherein the signal processor is configured to isolate a QRS complex as the selected time window from the ECG lead.

14. The system of claim 13, wherein the prediction extraction component extracts a fundamental frequency of the QRS complex as the predictor value.

15. The system of claim 13, wherein the parameter calculation component is configured to determine the parameter representing the likelihood that the patient will experience left ventricular dysfunction induced by the infranodal pacing from the predictor value and a biometric parameter that is not extracted from a frequency component of the QRS complex.

16. The system of claim 15, wherein the biometric parameter is duration of the QRS complex.

17. The system of claim 12, the parameter calculation component comprising a machine learning model trained on data from a plurality of previous patients.

18. A method comprising:
- applying infranodal pacing to a patient using a first pacing method;
- obtaining electrocardiogram (ECG) data representing the first pacing method from a set of electrodes as a first ECG lead;
- extracting a predictor value representing a change in a median frequency across a QRS complex of the first ECG lead, wherein the change in the median frequency is determined by dividing the QRS complex of the ECG lead into a plurality of subregions, determining a median frequency for each subregion, and calculating one of a slope of the median frequency across the plurality of subregions and a difference between the median frequency of a first selected subregion and a second selected subregion;
- determining a fitness parameter for the first pacing method from at least the first predictor value, the fitness parameter representing a likelihood that the infranodal pacing using the first pacing method will induce left ventricular dysfunction in the patient; and
- selecting a second pacing method for the patient if the fitness parameter does not meet a threshold value.

* * * * *